(12) United States Patent
Purcell et al.

(10) Patent No.: US 7,779,844 B2
(45) Date of Patent: Aug. 24, 2010

(54) SELF-FITTING DEVICE FOR LOCATION IN AN EAR CANAL

(75) Inventors: Ricky W. Purcell, Alpharetta, GA (US); Gregory J. Rajala, Neenah, WI (US); Ki Bok Song, Des Plaines, IL (US); Scott M. Belliveau, Plainfield, IL (US); Sena S. Corbin, Morton Grove, IL (US); Toriono A. Granger, Chicago, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 81 days.

(21) Appl. No.: 11/639,743

(22) Filed: Dec. 15, 2006

(65) Prior Publication Data

US 2008/0144871 A1 Jun. 19, 2008

(51) Int. Cl.
*A61F 11/00* (2006.01)
(52) U.S. Cl. .................................... 128/865; 128/864
(58) Field of Classification Search ......... 128/864–868; 181/128–130, 135; 623/10; 381/322, 328–329, 381/72
See application file for complete search history.

(56) References Cited

U.S. PATENT DOCUMENTS

| 2,246,736 A | 6/1941 | Knudsen |
| 2,824,558 A | 2/1958 | Michael et al. |
| 2,850,012 A | 9/1958 | Becker |
| 2,876,767 A | 3/1959 | Wasserman |
| 3,123,069 A | 3/1964 | Laisne et al. |
| 3,736,929 A | 6/1973 | Mills |
| 4,060,080 A | 11/1977 | Akiyama |
| 4,133,984 A | 1/1979 | Akiyama |
| 4,582,053 A | 4/1986 | Wilson |
| 4,913,165 A | 4/1990 | Fishgoyt |
| D364,455 S | 11/1995 | Krause |
| D366,313 S | 1/1996 | Krause |
| D366,696 S | 1/1996 | Krause |
| 5,483,027 A | 1/1996 | Krause |
| 6,256,396 B1 | 7/2001 | Cushman |
| 6,942,696 B1 * | 9/2005 | White et al. .................. 623/10 |
| 2004/0258263 A1 * | 12/2004 | Saxton et al. ............... 381/328 |

(Continued)

FOREIGN PATENT DOCUMENTS

EP    0 955 026 A1    11/1999

(Continued)

*Primary Examiner*—Patricia M Bianco
*Assistant Examiner*—Keri J Nicholson
(74) *Attorney, Agent, or Firm*—Nancy M. Klembus

(57) ABSTRACT

Self-fitting device for location in ear canal, including first end portion joined with second end portion. First end portion including first resilient bladder and first chamber of fluid and second end portion including second resilient bladder and second chamber of fluid. The bladders are in communication via the chambers. First bladder is deformable between at-rest position to in-ear position to insertion position such that first bladder has first cross-sectional area in at-rest position, second cross-sectional area in in-ear position and third cross-sectional area in insertion position. First cross-sectional area is greater than second cross-sectional area which is greater than third cross-sectional area. Second bladder is deformable to cause first bladder to be deformed from at-rest position to insertion position before device is located in ear canal.

17 Claims, 5 Drawing Sheets

U.S. PATENT DOCUMENTS

2008/0264428 A1  10/2008  Purcell et al.

FOREIGN PATENT DOCUMENTS

| EP | 1276443 B1 | 3/2006 |
|---|---|---|
| EP | 1 653 776 A2 | 5/2006 |
| GB | 1 423 194 A | 1/1976 |
| GB | 2 323 295 A | 9/1998 |
| JP | 06-343659 A | 12/1994 |
| JP | 10-094615 A | 4/1998 |
| JP | 2002-000637 A | 1/2002 |
| WO | WO 98/25558 A1 | 6/1998 |
| WO | WO 2004/100608 A2 | 11/2004 |
| WO | WO 2008/075221 A1 | 6/2008 |

* cited by examiner

SELF-FITTING DEVICE FOR LOCATION IN AN EAR CANAL

BACKGROUND OF THE INVENTION

The present invention relates generally to devices for location in an ear canal, and more particularly to such devices being self-fitting and used for sound optimization such as noise reduction and/or acoustic enhancement.

The need for adequate hearing protection in high noise environments has long been recognized among those concerned with health and safety issues, and much effort has gone into providing such protection. However, most experts in this field would acknowledge that this effort has not been very successful. Protective devices have proliferated yet remained mediocre in performance. Workers in high noise environments who should use these devices often do not, or use them only under duress from their employers. Individuals that work in high noise environments rarely understand that the effects of high noise exposure are not limited to the moment but are cumulative as well. The lack of worker compliance with safety rules is exacerbated by the fact that currently available hearing protection devices are often uncomfortable, clumsy to use, and/or perform poorly. Fortunately, as hearing protection devices become more comfortable and perform better, worker compliance with their use should also improve.

For example, existing disposable foam ear plugs are uncomfortable for wearers with small ear canals, are difficult to properly insert, must be completely removed if noise reduction is unwanted for a brief period (e.g. conversation), and/or cause discomfort by creating a vacuum in the ear canal during removal. Existing disposable foam ear plugs require the user to compress the area of the plug and insert it into the ear canal where it then attempts to re-expand. This method can cause discomfort for people with small ear canals in that the more compressed the ear plug, the greater its exerted force toward re-expansion. Further, existing disposable foam ear plugs require the user to roll the foam between their fingers to compress the foam to a sufficient area for proper insertion. If this step is not done, or is insufficiently done, the ear plug is often inserted improperly so as to not provide optimal protection. Also, if the user has dirty hands when compressing the ear plug, dirt and/or germs are then put into the ear canal with the inserted ear plug.

Further, existing disposable foam ear plugs must be completely removed if the user needs increased use of their hearing facilities for a brief period such as engaging in conversation with a coworker. This could lead to improper reinsertion if the earplugs are removed or misunderstanding of potentially important information if not removed. Also, existing disposable foam ear plugs are sealed against the wall of the ear canal in use and at the moment of removal. This causes a vacuum within the ear canal as the ear plugs are removed, and make removal difficult and/or uncomfortable. And, existing foam ear plugs are often designed for one time use.

Accordingly, while various types of in-ear devices exist in the art, there remains a need for an in-ear device that helps overcome one or more of the aforementioned problems. The applicants have surprisingly invented such a device, as discussed further herein.

SUMMARY OF THE INVENTION

Various definitions used throughout the specification and claims are provided first, followed by a description of various aspects of the invention.

As used herein, "resilient" means that property of a material or composite material that permits it to be deformed in size and/or shape and then recover at least about 80% of its original size and shape after removal of the force causing the deformation.

As used herein, "non-resilient" means the opposite of resilient.

In one aspect of the present invention, there is provided a self-fitting device for location in an ear canal. The device includes a first end portion joined with a second end portion, the first end portion including a first resilient bladder and the second end portion including a second resilient bladder. A first chamber of fluid is defined inside the first bladder and is sealed from an environment outside the device. A second chamber of fluid is defined inside the second resilient bladder and is sealed from the environment outside the device. The second resilient bladder is in communication with the first resilient bladder via communication of the second chamber with the first chamber. The first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position. The first cross-sectional area is greater than the second cross-sectional area and the second cross-sectional area is greater than the third cross-sectional area. The second resilient bladder is deformable such that deformation of the second resilient bladder causes the first resilient bladder to be deformed from the at-rest position to the insertion position before the device is located in the ear canal.

In another aspect of the present invention, there is provided a self-fitting device for location in an ear canal. The device includes first end portion joined with a second end portion, the first end portion including a first resilient bladder and the second end portion including a second resilient bladder. A first chamber of fluid is defined inside the first bladder and is sealed from an environment outside the device. A second chamber of fluid is defined inside the second resilient bladder and is sealed from the environment outside the device. The second resilient bladder is in communication with the first resilient bladder via communication of the second chamber with the first chamber. The first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position. The first cross-sectional area is greater than the second cross-sectional area and the second cross-sectional area is greater than the third cross-sectional area. The second resilient bladder is deformable such that deformation of the second resilient bladder causes the first resilient bladder to be deformed from the at-rest position to the insertion position. A plunger is in communication with the first and second chambers such that deformation of the second resilient bladder exerts pressure on the plunger causing the plunger to move away from the second chamber and thereby assists to deform the first resilient bladder. The plunger includes a head and a shaft joined to the head, with the shaft having an end spaced from the head and the end touching the first resilient bladder at least when the first resilient bladder is deformed.

In still another aspect of the present invention, there is provided a self-fitting device for location in an ear canal. The device includes first end portion joined with a second end portion, the first end portion including a first resilient bladder and the second end portion including a second resilient bladder. A first chamber of fluid is defined inside the first bladder and is sealed from an environment outside the device. A second chamber of fluid is defined inside the second resilient bladder and is sealed from the environment outside the device. The second resilient bladder is in communication with the first resilient bladder via communication of the second chamber with the first chamber. The first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position. The first cross-sectional area is greater than the second cross-sectional area and the second cross-sectional area is greater than the third cross-sectional area. The second resilient bladder is deformable such that deformation of the second resilient bladder causes the first resilient bladder to be deformed from the at-rest position to the insertion position. A plunger is in communication with the first and second chambers such that deformation of the second resilient bladder exerts pressure on the plunger causing the plunger to move away from the second chamber and thereby assists to deform the first resilient bladder. The plunger includes a core surrounded by a sheath in sliding relationship therewith.

Other features of the invention relate to particular configurations of the first and second bladders relative to one another when in the various at-rest, in-ear and insertions positions; and, particular structures for deforming the bladders between these positions.

Still other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the self-fitting device for location in an ear canal that is the present invention.

BRIEF DESCRIPTION OF THE DRAWINGS

Corresponding reference characters indicate corresponding parts throughout the drawings.

DETAILED DESCRIPTION

Figure 1:
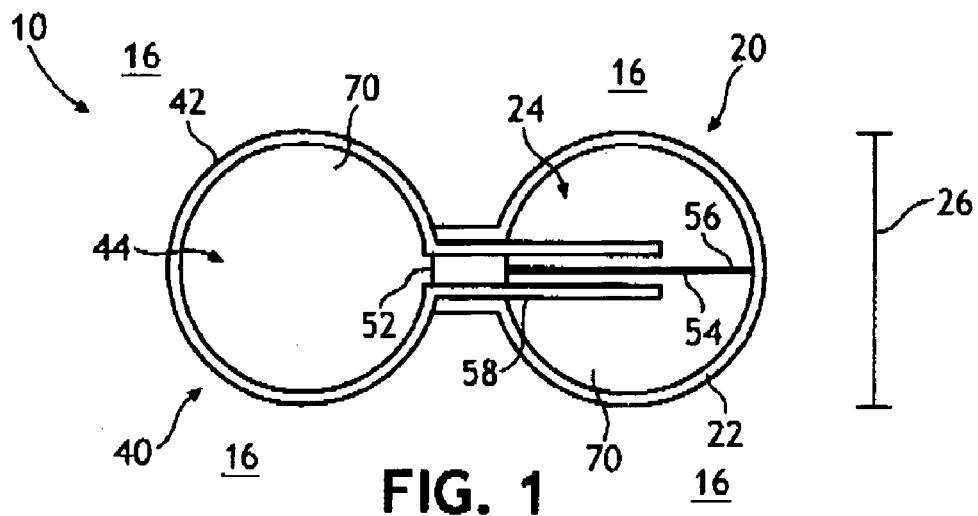
FIG. 1 is a cross-sectional side view of the present invention in the at-rest position.
Figure 2:
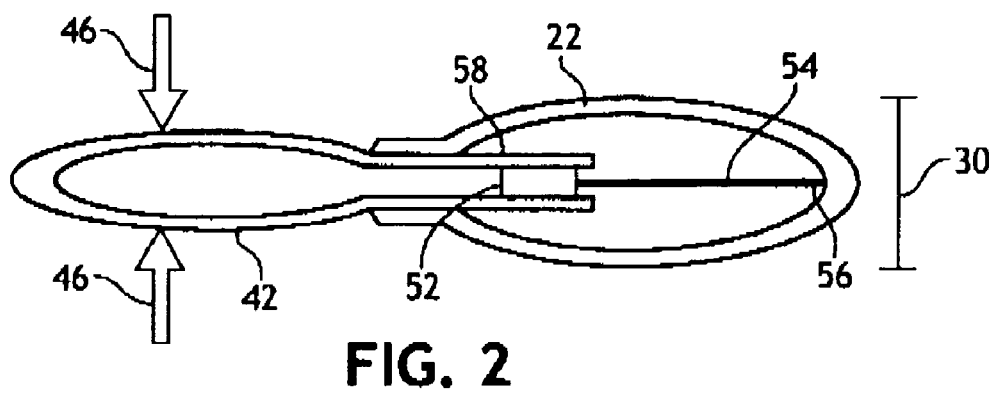
FIG. 2 is a cross-sectional side view of the device in FIG. 1, but now in the insertion position.
Figure 3:
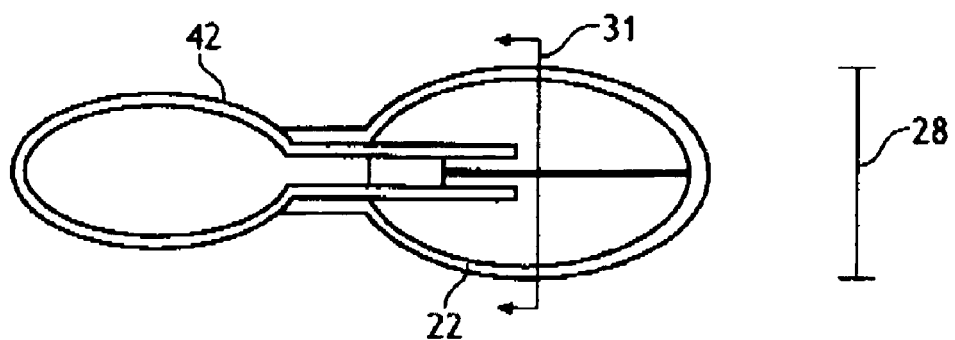
FIG. 3 is a is a cross-sectional side view of the device in FIG. 1, but now in the in-ear position.
Figure 4:
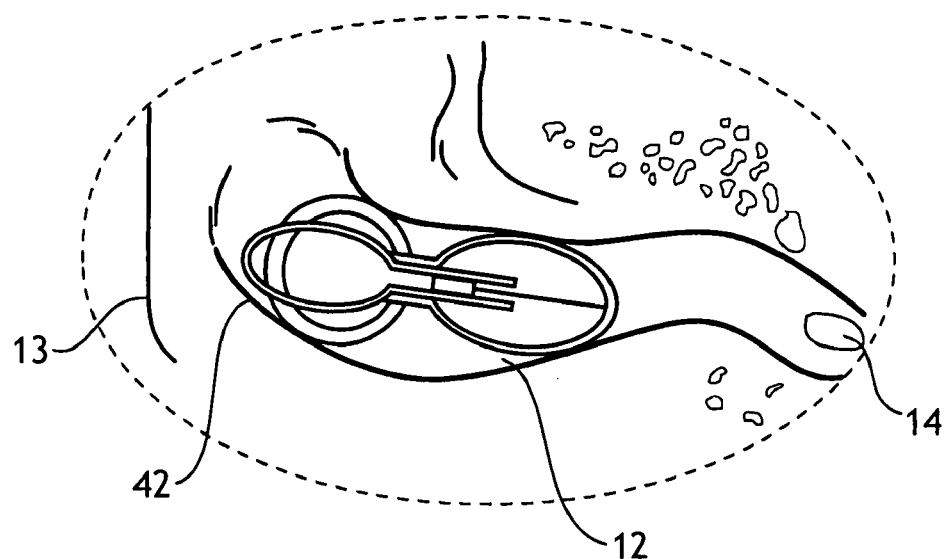
FIG. 4 is a cross-sectional side view of the device in FIG. 3, and now located in the ear canal.
Figure 5:
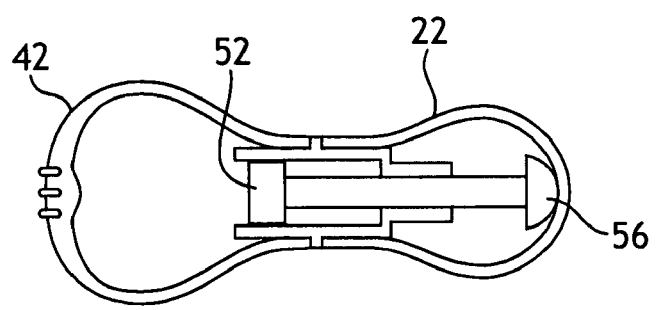
FIG. 5 is a cross-sectional side view of the present invention in the at-rest position.
Figure 6:
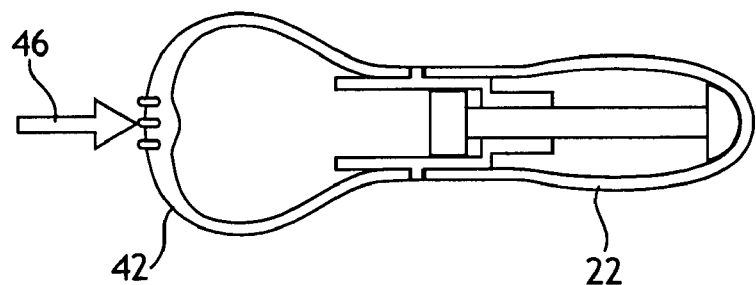
FIG. 6 is a cross-sectional side view of the device in FIG. 5, but now in the insertion position.
Figure 7:
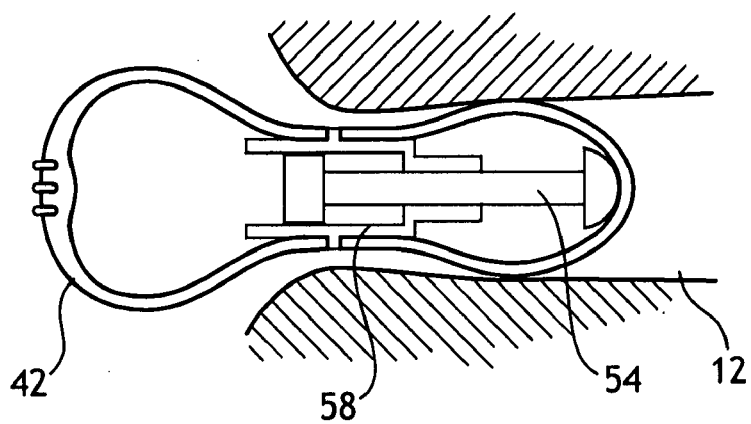
FIG. 7 is a cross-sectional side view of the device in FIG. 5, but now in the in-ear position and located in the ear canal.

Referring now to the drawings and in particular to FIGS. 1-4, for example, there is depicted a self-fitting device 10 for location in an ear canal 12. Particularly in FIG. 4 is seen outer ear 13 joined to the portion of the ear canal through which the device 10 is first inserted for use, and ear drum 14 at the other end of the ear canal spaced from the device when inserted into the ear canal. Device 10 includes a first end portion 20 joined with a second end portion 40. First end portion 20 includes a first resilient bladder 22. Second end portion 40 includes a second resilient bladder 42. A first chamber 24 of fluid is defined inside first bladder 22 and can be sealed from an environment 16 outside device 10. Alternatively, chamber 24 need not be sealed from the environment. FIGS. 1-7 show chamber 24 as being both sealed or unsealed relative to the environment 16. A second chamber 44 of fluid is defined inside second resilient bladder 42 and is sealed from the environment 16 outside device 10. When chamber 24 is sealed from the environment, second resilient bladder 42 is in communication with first resilient bladder 22 via communication of second chamber 44 with first chamber 24.

The first resilient bladder 22 is deformable between an at-rest position (FIG. 1) to an in-ear position (FIG. 3) to an insertion position (FIG. 2) such that the first resilient bladder has a first cross-sectional area 26 in the at-rest position, a second cross-sectional area 28 in the in-ear position and a third cross-sectional area 30 in the insertion position. First cross-sectional area 26 is greater than second cross-sectional area 28, and second cross-sectional area 28 is greater than third cross-sectional area 30. The cross-sectional area is determined using the plane orthogonal to the length (longest dimension) of device 10 and parallel to respective area lines 26, 28, 30, and then measuring the largest area of the portion of the first resilient bladder that would engage (at-rest and insertion positions) or engages (in-ear position) the inside of the ear canal, taking view 31 (FIG. 3). The second resilient bladder 42 is deformable such that deformation of the second resilient bladder causes the first resilient bladder 22 to be deformed from the at-rest position to the insertion position.

In a particular suitable aspect, though not required, the second resilient bladder causes the first resilient bladder 22 to be deformed from the at-rest position to the insertion position before the device 10 is located in the ear canal 12. In a related suitable aspect, deformation of the second resilient bladder causes the first resilient bladder to be deformed from the at-rest position then to the in-ear position and then to the insertion position. Stated still more suitably, and as happens in practice, the device can operate such that an external pressure 46 applied to the second resilient bladder (e.g., a squeezing force from somewhere around bladder 42, e.g., by a user's hand or the like) deforms the second resilient bladder, i.e., incrementally, thereby causing the first resilient bladder to, i.e., incrementally, be deformed from the at-rest position then to the in-ear position then to the insertion position and then back to the in-ear position when the external pressure 46 is removed from the second resilient bladder. At this point, the device 10 would be located in ear canal 12 in a partially expanded condition to block the ear canal for sound optimization such as noise reduction and/or acoustic enhancement. In particular, the in-ear position is determined by the user's particular ear canal shape and size and is therefore self-fitting or customizable.

Deformation of the first resilient bladder may be achieved in a variety of ways. For example, When chamber 24 is sealed from the environment, deformation of second resilient bladder 42 causing fluid to leave second chamber 44 and enter first chamber 24 and thereby cause first resilient bladder 22 to be deformed from the at-rest position to the insertion position (i.e., and on its way through the in-ear position). The fluid could be a gas 70 (FIGS. 1-7 and 11-16) or a liquid 72 (FIGS. 8-10), including gels and micro particles that act like a fluid. As seen in FIGS. 1-10, the communication between chambers 24 and 44 occurs for the common portions on either side of head 52. Thus, while communication between the chambers for the devices in FIGS. 1-10 can occur, it is much more limited than for chambers 24 and 44 of the devices in FIGS. 11-16, where communication of fluid in the chambers is much greater.

Figure 8:
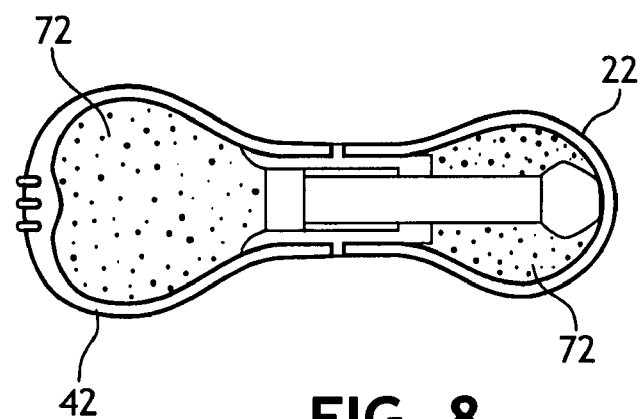
FIG. 8 is a cross-sectional side view of the present invention in the at-rest position.
Figure 9:
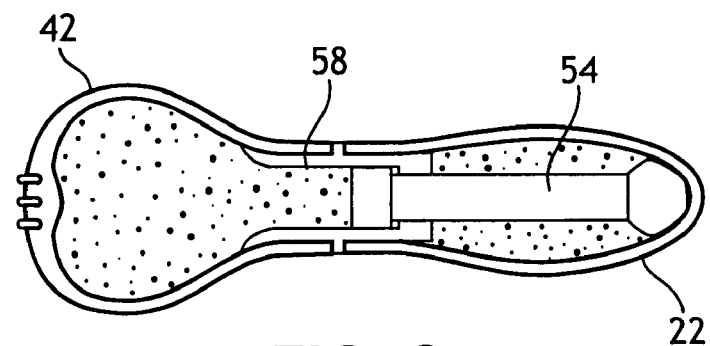
FIG. 9 is a cross-sectional side view of the device in FIG. 8, but now in the insertion position.
Figure 10:
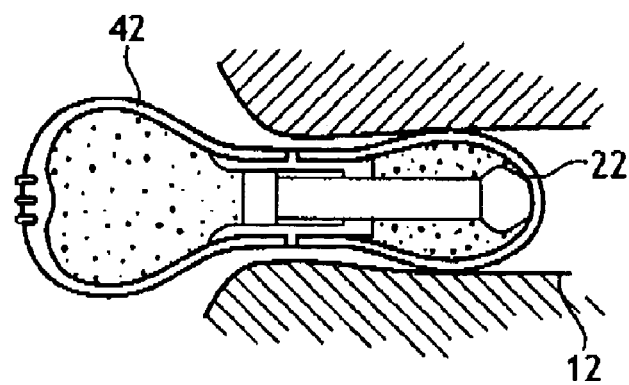
FIG. 10 is a cross-sectional side view of the device in FIG. 8, but now in the in-ear position and located in the ear canal.

As another example of how to deform first resilient bladder 22, it may be that a plunger is in communication with first and second chambers 24, 44 such that deformation of second resilient bladder 42 exerts pressure on the plunger causing the plunger to move away from the second chamber and thereby assist to deform the first resilient bladder 22. More particularly for example, the plunger may be a head 52 and a shaft 54 joined to the head, with the shaft 54 having an end 56 spaced from the head and the end touching the first resilient bladder 22 at least when the first resilient bladder is deformed. The shaft 54 may be spaced from the bladder 22 (FIG. 1) when in the at-rest position, or abutting the bladder (FIG. 5) or joined with the bladder (FIG. 8). And alternatively for example, the plunger may be a core 58 surrounded by a sheath 60 in sliding relationship therewith. Additionally, it may be that the core 58 is joined with second resilient bladder 42 and sheath 60 is joined with first resilient bladder 22. Still alternately, the plunger may include core 58 in sliding relationship with head 52, where the core may be joined to second resilient bladder 42.

Figure 11:
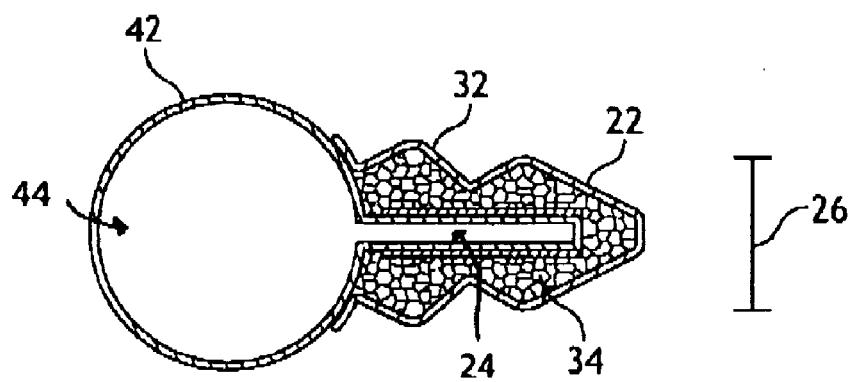
FIG. 11 is a cross-sectional side view of the present invention in the at-rest position.
Figure 12:
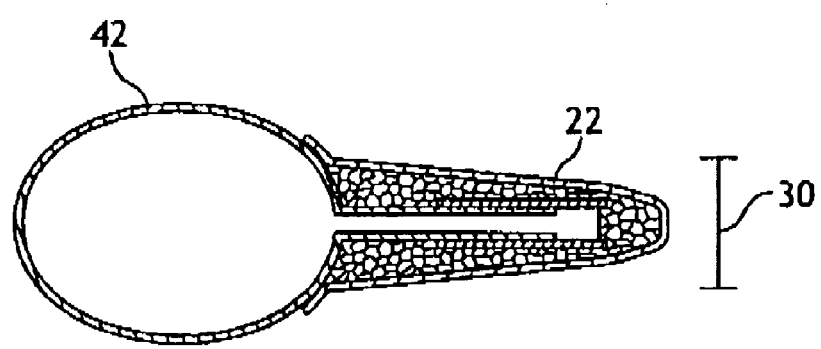
FIG. 12 is a cross-sectional side view of the device in FIG. 11, but now in the insertion position.
Figure 13:
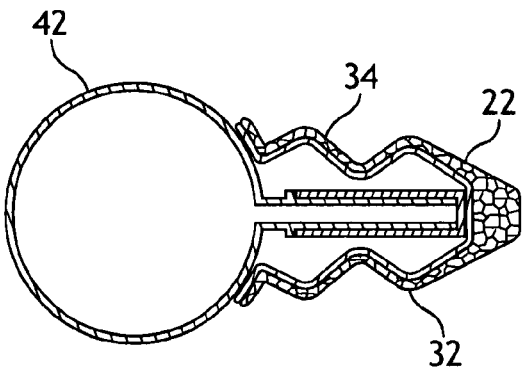
FIG. 13 is a cross-sectional side view of the present invention in the at-rest position.
Figure 14:
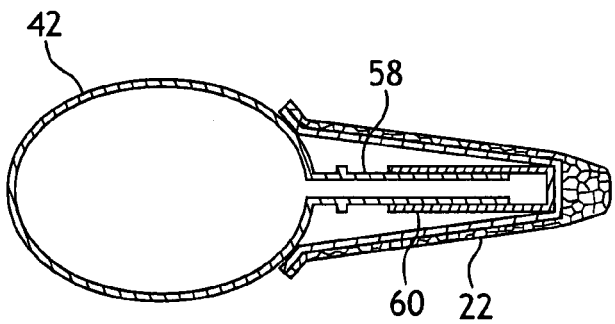
FIG. 14 is a cross-sectional side view of the device in FIG. 13, but now in the insertion position.
Figure 15:
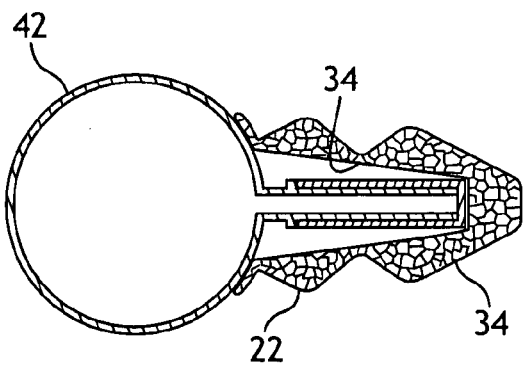
FIG. 15 is a cross-sectional side view of the present invention in the at-rest position.
Figure 16:
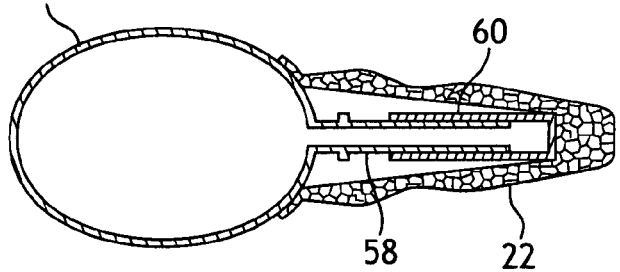
FIG. 16 is a cross-sectional side view of the device in FIG. 15, but now in the insertion position.

The resilient bladders made be made of a homogeneous material or a composite material, and may include one or more layers. Referring specifically to FIGS. 11-16 there are depicted some multi layer devices 10. In FIGS. 11 and 12, the first resilient bladder 22 comprises a non-resilient material layer 32 surrounding a resilient material layer 34. In FIGS. 13 and 14, the first resilient bladder 22 comprises a resilient material layer 34 surrounding a non-resilient material layer 32. In FIGS. 15 and 16, the first resilient bladder 22 comprises a resilient material layer 34 surrounding a resilient material layer 34. Further in regards to these Figures, it may be further suitable to the invention for the first resilient bladder 22 to maintain an accordion shaped outer surface when in the at-rest position.

Still referring, primarily, to FIGS. 11-16, bladder 22 may be made of a polyurethane foam with a "skin" formed on the outside. Bladder 42 may be made from a flexible material that is readily blow moldable into a bulb that dose not permanently deform stressed by squeezing. Examples could be polyurethane, santoprene, polyethylene, or polypropylene. The core 58 may be formed with bladder 42, and may have the sheath 60 molded to the outside. The sheath may be molded from a polymer that will not knit to the bladder or core material. Examples might be santoprene, silicone, or polypropylene with high amounts of a slip agent.

Steps in making the device of FIGS. 11-16 may be as follows: injection molding a plastic pre-form the bladder 42 with core 58; the sheath 60 is then molded on the outside of core 58; air is blown into the open end of the core and sheath to form the bladder 42; foam material is molded over the sheath and bladder 42 form bladder 22. The urethane foam must bond itself to the bladder 42 material. Alternatively, bladder 42 may be molded separately from the bladder 22. In this case, the two bladders would then be glued together in final form.

Without being limited to a particular theory of understanding or noted advantageous features, the following features are noted. The reduction in the cross-sectional area is converted into additional length of bladder 22 thus reducing the diametrical force exerted on small ear canals, thereby enhancing comfort even for smaller ear canals. Also, this diametrical reduction is achieved more conveniently and more effectively thus increasing the likelihood of proper insertion and more optimal protection, for all size ear canals. When in use and acoustic enhancement is desired, squeezing the second resilient bladder reduces the cross-sectional area of the first bladder while device 10 is still inserted in the ear canal thus increasing the users hearing ability without requiring that device 10 be removed. For removal, since the cross-sectional area is reduced, it breaks the seal with the ear canal prior to removal, for a more comfortable removal. Also, with the features of the present invention it is made of sufficiently substantial materials and design so as to allow for multiple uses.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", an "the" and "said" are intended to mean that there are one or more of the elements. The terms "comprising", "including" and "having" are intended to be inclusive and mean that there may be additional elements other than the listed elements.

What is claimed is:

1. A self-fitting device for location in an ear canal, comprising:
    a first end portion joined with a second end portion, the first end portion locatable in an ear canal closer to an ear drum than the second end portion and the first end portion including a first resilient bladder and the second end portion including a second resilient bladder;
    a first chamber of fluid defined inside the first bladder and sealed from an environment outside the device;
    a second chamber of fluid defined inside the second resilient bladder and sealed from the environment outside the device, the second resilient bladder in communication with the first resilient bladder via communication of the second chamber with the first chamber;
    the first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position wherein the first cross-sectional area is greater than the second cross-sectional area and the second cross-sectional area is greater than the third cross-sectional area; and, the second resilient bladder is deformable such that deformation of the second resilient bladder causes fluid from the second chamber to move toward the first chamber and thereby causes the first resilient bladder to be deformed from the at-rest position to the insertion position before the device is located in the ear canal; and, further comprising a plunger, where the plunger is in communication with the first and second chambers such that deformation of the second resilient bladder exerts pressure on the plunger causing the plunger to move away from the second chamber and thereby assists to deform the first resilient bladder.

2. The device of claim 1 wherein deformation of the second resilient bladder causes the first resilient bladder to be deformed from the at-rest position then to the in-ear position and then to the insertion position.

3. The device of claim 1 wherein an external pressure applied to the second resilient bladder deforms the second resilient bladder thereby causing the first resilient bladder to be deformed from the at-rest position then to the in-ear position then to the insertion position and then back to the in-ear position when the external pressure is removed from the second resilient bladder.

4. The device of claim 1 wherein the plunger comprises a head and a shaft joined to the head and with the shaft having an end spaced from the head and the end touching the first resilient bladder at least when the first resilient bladder is deformed.

5. The device of claim 1 wherein the plunger comprises a core surrounded by a sheath in sliding relationship therewith.

6. The device of claim 5 wherein the core is joined with the second resilient bladder and the sheath is joined with the first resilient bladder.

7. The device of claim 1 wherein the fluid is a gas or a liquid.

8. A self-fitting device for location in an ear canal, comprising:
   a first end portion joined with a second end portion, the first end portion locatable in an ear canal closer to an ear drum than the second end portion and the first end portion including a first resilient bladder and the second end portion including a second resilient bladder;
   a first chamber of fluid defined inside the first bladder and sealed from an environment outside the device;
   a second chamber of fluid defined inside the second resilient bladder and sealed from the environment outside the device, the second resilient bladder in communication with the first resilient bladder via communication of the second chamber with the first chamber;
   the first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position wherein the first cross-sectional area is greater than the second cross-sectional area and the second cross-sectional area is greater than the third cross-sectional area;
   the second resilient bladder is deformable such that deformation of the second resilient bladder causes fluid from the second chamber to move toward the first chamber and thereby causes the first resilient bladder to be deformed from the at-rest position to the in-ear position; and,
   a plunger in communication with the first and second chambers such that deformation of the second resilient bladder exerts pressure on the plunger causing the plunger to move away from the second chamber and thereby assists to deform the first resilient bladder wherein the plunger comprises a head and a shaft joined to the head and with the shaft having an end spaced from the head and the end touching the first resilient bladder at least when the first resilient bladder is deformed.

9. The device of claim 8 wherein the end of the shaft is joined to the first resilient bladder.

10. The device of claim 8 comprising a core in sliding relationship with the head with the core joined to the second resilient bladder.

11. The device of claim 8 wherein an external pressure applied to the second resilient bladder deforms the second resilient bladder and thereby causing the first resilient bladder to be deformed from the at-rest position then to the in-ear position then to the insertion position and then back to the in-ear position when the external pressure is removed from the second resilient bladder.

12. A self-fitting device for location in an ear canal, comprising:
   a first end portion joined with a second end portion, the first end portion locatable in an ear canal closer to an ear drum than the second end portion and the first end portion including a first resilient bladder and the second end portion including a second resilient bladder;
   a first chamber of fluid defined inside the first bladder and sealed from an environment outside the device;
   a second chamber of fluid defined inside the second resilient bladder and sealed from the environment outside the device, the second resilient bladder in communication with the first resilient bladder via communication of the second chamber with the first chamber;
   the first resilient bladder is deformable between an at-rest position to an in-ear position to an insertion position such that the first resilient bladder has a first cross-sectional area in the at-rest position, a second cross-sectional area in the in-ear position and a third cross-sectional area in the insertion position wherein the first cross-sectional area is greater than the second cross-sectional area and the second cross-sectional area is greater than the third cross-sectional area;
   the second resilient bladder is deformable such that deformation of the second resilient bladder causes fluid from the second chamber to move toward the first chamber and thereby causes the first resilient bladder to be deformed from the at-rest position to the in-ear position; and,
   a plunger in communication with the first and second chambers such that deformation of the second resilient bladder exerts pressure on the plunger causing the plunger to move away from the second chamber and thereby assists to deform the first resilient bladder wherein the plunger comprises a core surrounded by a sheath in sliding relationship therewith.

13. The device of claim 12 wherein the core is joined with the second resilient bladder and the sheath is joined with the first resilient bladder.

14. The device of claim 12 wherein the first resilient bladder comprises a non-resilient material layer surrounding a resilient material layer.

15. The device of claim 12 wherein the first resilient bladder comprises a resilient material layer surrounding a non-resilient material layer.

16. The device of claim 12 wherein the first resilient bladder comprises a resilient material layer surrounding a resilient material layer.

17. The device of claim 12 wherein the first resilient bladder maintains an accordion shaped outer surface when in the at-rest position.

* * * * *